United States Patent
Kennington

(10) Patent No.: US 10,416,067 B2
(45) Date of Patent: Sep. 17, 2019

(54) METHOD FOR AIR BUBBLE DETECTION BETWEEN SAMPLES USING FLOW CYTOMETRY SCATTER WAVEFORM ANALYSIS

(71) Applicant: Essen Instruments, Inc., Ann Arbor, MI (US)

(72) Inventor: Aaron Bryce Kennington, Albuquerque, NM (US)

(73) Assignee: Essen Instruments, Inc., Ann Arbor, MI (US)

( * ) Notice: Subject to any disclaimer, the term of this patent is extended or adjusted under 35 U.S.C. 154(b) by 35 days.

(21) Appl. No.: 15/616,168

(22) Filed: Jun. 7, 2017

(65) Prior Publication Data

US 2017/0350802 A1    Dec. 7, 2017

Related U.S. Application Data

(60) Provisional application No. 62/346,739, filed on Jun. 7, 2016.

(51) Int. Cl.
| | |
|---|---|
| G01N 15/14 | (2006.01) |
| G01N 21/53 | (2006.01) |
| G01N 35/08 | (2006.01) |
| G01N 15/10 | (2006.01) |

(52) U.S. Cl.
CPC ......... *G01N 15/1404* (2013.01); *G01N 21/53* (2013.01); *G01N 35/08* (2013.01); *G01N 2015/1006* (2013.01)

(58) Field of Classification Search
CPC ............... G01N 15/1404; G01N 21/53; G01N 2015/1006
See application file for complete search history.

(56) References Cited

U.S. PATENT DOCUMENTS

| | | |
|---|---|---|
| 6,878,556 B2 | 4/2005 | Sklar et al. |
| 6,890,487 B1 | 5/2005 | Sklar et al. |
| 7,368,084 B2 | 5/2008 | Sklar et al. |

(Continued)

FOREIGN PATENT DOCUMENTS

| | | |
|---|---|---|
| GB | 1407764 A | 9/1975 |
| GB | 2099575 A | 12/1982 |

(Continued)

OTHER PUBLICATIONS

International Search Report for PCT/US2017/036317, dated Oct. 25, 2017.

*Primary Examiner* — Dominic J Bologna
(74) *Attorney, Agent, or Firm* — McDonnell Boehnen Hulbert & Berghoff LLP

(57) ABSTRACT

A method for detecting a separation gas in a fluid flow stream is provided herein. In one example, a voltage output signal is generated by a scatter detector of a flow cytometer as a flow stream of a plurality of gas-separated samples passes through the flow cytometer. The voltage output signal is sampled, and a timestamp and a voltage value are recorded for each sampled voltage of the voltage output signal that is greater than a separation gap threshold. In some examples the separation gap threshold is at least two times greater than a maximum voltage output of the samples. Flow cytometry systems including software configured to perform these method steps are also described.

23 Claims, 10 Drawing Sheets

(56) References Cited

U.S. PATENT DOCUMENTS

| | | | |
|---|---|---|---|
| 7,842,244 B2 | 11/2010 | Sklar et al. | |
| 8,021,872 B2 | 9/2011 | Sklar et al. | |
| 8,268,571 B2 | 9/2012 | Sklar et al. | |
| 8,976,352 B2* | 3/2015 | Muraki | G01N 21/64 356/338 |
| 9,476,101 B2* | 10/2016 | Pregibon | C12Q 1/6816 |
| 9,551,644 B2 | 1/2017 | Kennington et al. | |
| 9,797,917 B2 | 10/2017 | Barnes et al. | |
| 10,041,884 B2* | 8/2018 | Fujioka | G06F 19/24 |
| 2002/0170365 A1* | 11/2002 | Sklar | G01N 15/1459 73/865.5 |
| 2005/0162648 A1* | 7/2005 | Auer | G01N 15/14 356/318 |
| 2010/0197512 A1 | 8/2010 | Trinkle et al. | |
| 2012/0061584 A1 | 3/2012 | Trinkle et al. | |
| 2012/0309635 A1 | 12/2012 | Trinkle et al. | |
| 2013/0210672 A1 | 8/2013 | Sklar et al. | |
| 2014/0005537 A1* | 1/2014 | Asami | A61B 5/0095 600/431 |
| 2015/0346075 A1 | 12/2015 | Andreev et al. | |
| 2018/0253034 A1* | 9/2018 | Doshida | G03G 15/105 |

FOREIGN PATENT DOCUMENTS

| | | |
|---|---|---|
| JP | H02176543 A | 7/1990 |
| JP | 2007225335 A | 9/2007 |

\* cited by examiner

METHOD FOR AIR BUBBLE DETECTION BETWEEN SAMPLES USING FLOW CYTOMETRY SCATTER WAVEFORM ANALYSIS

RELATED APPLICATIONS

This application claims the benefit of priority to U.S. Provisional Application No. 62/346,739 entitled "Method for air bubble detection between samples using flow cytometry forward scatter waveform analysis," filed on Jun. 7, 2016, the contents of which are hereby incorporated by reference in their entirety.

BACKGROUND

High-throughput flow cytometry systems use a pump system to fill a sample tubing line with a stream of discrete sample particle suspensions aspirated from wells of a microplate and separated one from the other by air bubble gaps. The entire sample stream is continuously delivered to the flow cytometer so that data from all the samples in the microplate are acquired and stored in a single data file. A high resolution time parameter is also recorded during data acquisition. Temporal gaps in particle detection are created in the data stream by the passage of the air gaps, allowing the individual particle suspensions to be distinguished and separately evaluated when plotted in conjunction with the time parameter. Based on this temporal distribution, data peaks are identified and assigned to individual wells of the microplate. However, in many cases, these temporal distributions are not sufficient to accurately identify individual sample wells, and identification errors sometimes occur.

SUMMARY

Methods and systems for detecting air bubbles in a continuous fluidic stream of samples separated by air bubbles are disclosed herein. In one example, the scatter waveform output of the scatter detector of the flow cytometer is used to detect the air bubbles.

Some embodiments of the present disclosure provide a method for: generating, with a scatter detector, a voltage output signal as a flow stream comprising a plurality of samples, each sample separated by a separation gas, passes through a flow cytometer for a period of time; sampling the voltage output signal; and recording a timestamp and a voltage value for each sampled voltage of the voltage output signal that is greater than a separation gap threshold. The method may further include the steps of: prior to the generating step, moving the plurality of samples comprising particles into the flow stream; inserting the separation gas between adjacent ones of said plurality of samples to separate said samples from each other in said flow stream, said flow stream thereby constituting a gas-separated sample flow stream; guiding said fluid-separated sample flow stream including the separated samples and the separation fluid to and through the flow cytometer; and continuously operating the flow cytometer to focus the gas-separated flow stream and to detect scattered light by the scatter detector as the fluid flow stream passes through the flow cytometer. In further embodiments, the method may include the step of: prior to the moving step, obtaining a plurality of samples from a plate having a plurality of sample wells, wherein each sample of the plurality of samples is obtained from a respective well of the plurality of wells.

Embodiments of the present disclosure further include a non-transitory computer readable medium having stored therein instructions that are executable to cause a processor to perform the methods described herein.

Further embodiments of the present disclosure include a system comprising: a flow cytometer comprising a scatter detector; a processor in communication with the output of the scatter detector; and a non-transitory computer readable medium having stored therein instructions that are executable to cause the processor to perform the methods described herein.

DETAILED DESCRIPTION

Figure 1A:
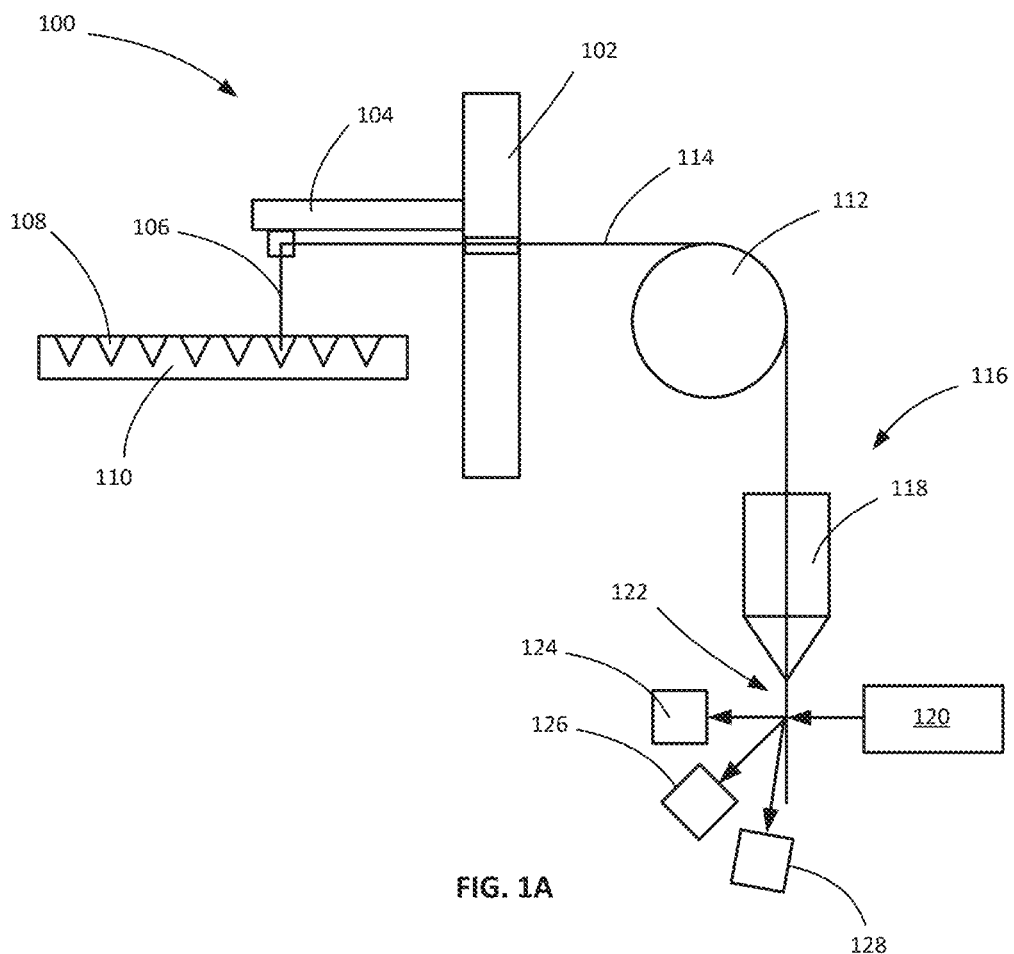
FIG. 1A is a schematic view of a flow cytometry apparatus.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively.

The description of embodiments of the disclosure/examples is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All embodiments of any aspect of the invention can be used in combination, unless the context clearly dictates otherwise.

For the purposes of the present invention, the term "sample" as used herein refers to any quantity of liquid which may contain particles of interest or marker particles that are detectable by a particle analyzer. More specifically a sample may include a fluid solution or suspension containing particles of interest or marker particles to be detected and/or analyzed using a method and/or apparatus disclosed herein. The particles of interest in a sample may be tagged, such as with a fluorescent tag. The particles of interest may also be bound to a bead, a receptor, or other useful protein or polypeptide, or may just be present as free particles, such as particles found naturally in a cell lysate, purified particles from a cell lysate, particles from a tissue culture, etc. The sample may include chemicals, either organic or inorganic, used to produce a reaction with the particles of interest. When the particles of interest are biomaterials, drugs may be added to the samples to cause a reaction or response in the biomaterial particles. The chemicals, drugs or other additives may be added to and mixed with the samples when the samples are in sample source wells or the chemicals, drugs or other additives may be added to the samples in the fluid flow stream after the samples have been uptaken by the autosampler.

As used herein, the term "biomaterial" refers to any organic material obtained from an organism, either living or dead. The term "biomaterial" also refers to any synthesized biological material such as synthesized oligonucleotides, synthesized polypeptides, etc. The synthesized biological material may be a synthetic version of a naturally occurring biological material or a non-naturally occurring biological made from portions of naturally occurring biological materials, such as a fusion protein, or two biological materials that have been bound together, such as an oligonucleotide, such as DNA or RNA, bound to a peptide, either covalently or noncovalently, that the oligonucleotide does not normally bind to in nature.

As used herein, the term "oligonucleotide" refers to any oligonucleotide, including double and single-stranded DNA, RNA, PNAs (peptide nucleic acids) and any sequence of nucleic acids, either natural or synthetic, derivatized or underivatized.

As used herein, "peptide" refers to all types of peptides and conjugated peptides including: peptides, proteins, polypeptides, protein sequences, amino acid sequences, denatured proteins, antigens, oncogenes and portions of oncogenes.

As used herein, the term "organism" refers not only to animals, plants, bacteria, viruses, etc. but also to cell cultures, reproduced oligonucleotides, etc. made from organic material obtained from animals, plants, bacteria, viruses, etc.

As used herein, the term "drug" refers to any type of substance that is commonly considered a drug. A drug may be a substance that acts on the central nervous system of an individual, e.g. a narcotic, hallucinogen, barbiturate, or a psychotropic drug. For the purposes of the present invention, a drug may also be a substance that kills or inactivates disease-causing infectious organisms. In addition, a drug may be a substance that affects the activity of a specific cell, bodily organ or function. A drug may be an organic or inorganic chemical, a biomaterial, etc.

As used herein, an "aliquot" is a sip of a sample taken from a well via a probe of a flow cytometer.

As used herein, the term "conduit" refers to device such as a tube, channel, etc. through which a fluid stream flows. A conduit may be composed of several separate devices, such as a number of connected or joined pieces of tubing or a single piece of tubing, alone or in combination with channels or other different devices. In various embodiments, a conduit may include any tube that may be used with a peristaltic pump that has compression characteristics that allow a peristaltic pump to move samples separated by a separation gas or aliquots of marker particles through the tube at a speed of at least 6 samples per minute without causing adjacent samples to mix with each other.

As used herein "marker particles" may include control particles, beads or micro beads and further refers to one or more particles detectable by a flow cytometer system (for example, a system as described in U.S. Pat. No. 6,878,556 and WO2010005617) that may uptake from a sample container an aliquot of a sample suspected of having therein particles of interest to be analysed.

For the purposes of the present invention, the term "particles" as used herein refers to small objects that may be present in a sample and detected using a flow cytometry apparatus, including, but not limited to biological particles, such as molecules, cells, proteins, protein aggregates, cellular components such as nuclei, and mitochondrion, organisms, including microbes and viruses, microspheres, microbeads, and synthetic particles, such as chemical compounds and chemical aggregates, etc.

For the purposes of the present invention, the term "sample" refers to a fluid solution or suspension which may contain particles of interest.

For the purposes of the present invention, the term "well" as used herein refers to any structure which contains a sample to be analysed, a control or an aliquot of marker particles.

For the purposes of the present invention, the terms "plate," "microplate," and "microtiter plate" as used herein refer to a structure which contains a sample to be analysed, a control, or an aliquot of marker particles.

For the purposes of the present invention, the term "about" means +/−5% of the recited parameter.

For the purposes of the present invention, the term "detector" refers to any detector capable of detecting scattered light, including photomultiplier tubes (PMTs) and single-photon avalanche diodes (SPADs).

For the purposes of the present invention, the term "separation gas" refers to any gas such as air, an inert gas, or fluid etc. that can be used to form a gas bubble or immiscible fluid between adjacent samples or between a sample and a buffer fluid. An immiscible fluid is a fluid that will not substantially mix with and contaminate a sample.

For the purposes of the present invention, the term "adjacent samples" refers to two samples in a fluid flow stream that are separated from each other only by a separation gas, such as an air bubble.

For the purposes of the present invention, the term "flow cytometer" includes any flow cytometry apparatus, including, but not limited to, the flow cytometers are described in U.S. Pat. Nos. 5,895,764; 5,824,269; 5,395,588; 4,661,913; the entire contents and disclosures of which are hereby incorporated by reference. In the flow cytometer, samples may be sorted on a particle by particle basis using known methods.

The present disclosure describes a novel system and method for detecting air bubbles in a continuous fluidic stream of samples separated by air bubbles using the scatter waveform output of the flow cytometer detector.

FIG. 1A illustrates an exemplary flow cytometry apparatus 100 for use in connection with the present invention. Flow cytometry apparatus 100 includes a conventional autosampler 102 having an adjustable arm 101 on which is mounted a hollow probe 106. As arm 104 moves back and forth (left and right in FIG. 1A) and side to side (into and out of the plane of FIG. 1A), probe 106 is lowered into individual source wells 108 of a well plate 110 to obtain a sample comprising particles (which may be tagged with a fluorescent tag (not shown in FIG. 1A)) to be analyzed using flow cytometry apparatus 100. In between in-taking sample material from each of source wells 108, probe 106 is allowed to intake aliquots of a separation fluid (such as air), thereby forming a separation bubble between successive samples in the fluid flow stream.

Once a sample is picked up by probe 106, it is introduced into a fluid flow stream and a peristaltic pump 112 forces the sample through a conduit 114 that extends from autosampler 102 through peristaltic pump 112 and into a flow cytometer 116 including a flow cell 118 and a laser interrogation device 120. The flow cell 118 may be continuously operated to focus the fluid flow stream and to analyze the particles in each of the plurality of samples as the fluid flow stream passes through the flow cytometer. Laser interrogation device 120 examines individual samples flowing from flow cell 118 at a laser interrogation point 122.

Figure 1B:
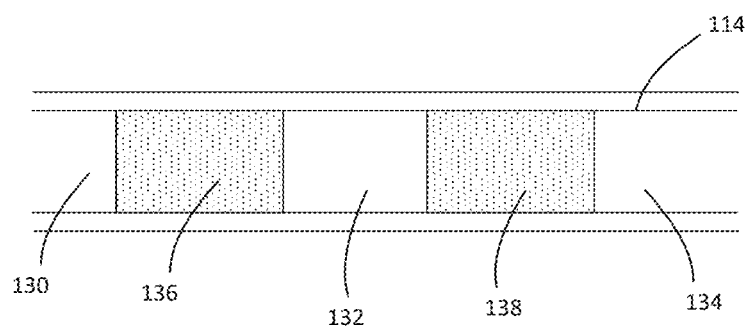
FIG. 1B is a cross-sectional schematic view of immediately adjacent samples in a conduit of the flow cytometry apparatus of FIG. 1A.

FIG. 1B illustrates series of samples 130, 132 and 134 separated from each other by separation bubbles 136 and 138 in conduit 114, forming a bubble-separated fluid flow stream. In FIG. 1B, sample 130 is immediately adjacent to sample 132, and sample 132 is immediately adjacent to sample 134. When samples 130, 132 and 134 pass through laser interrogation point 122, the particles in the samples are sensed by flow cytometer 116. Forward scattered light is detected by a forward scatter detector 124. Fluorescence emitted from tagged particles in the flow cell is detected by a fluorescence detector 126. Side scattered light is detected by a side scatter detector 128. In contrast, when air bubbles 136 and 138 pass through laser interrogation point 122, no particles are sensed. Therefore, a graph of the data points of fluorescence sensed versus time for a series of samples analyzed using a flow cytometer will form distinct groups, each aligned with the time that a sample containing particles passes through the laser interrogation point. Such graphs can be generated by the output of both the forward scatter detector 124, the fluorescence detector 126, and/or the side scatter detector 128.

Correctly identifying the sample well from which each sample was taken is important in analysis and use of the flow cytometer output data. In some high-throughput flow cytometry system methods, the sampling protocol, including parameters such as the probe sip time (the duration that the probe is in a well), probe up time (the amount of time the probe pauses out of a well to draw in air), multiwell shakes and rinse steps, the sampling order, as well as the height of event peaks and the spacing between them, are used to segment the data file for an entire microtiter plate into individual well data. However, even with utilizing these elements, well identification errors still occur.

Figure 2:
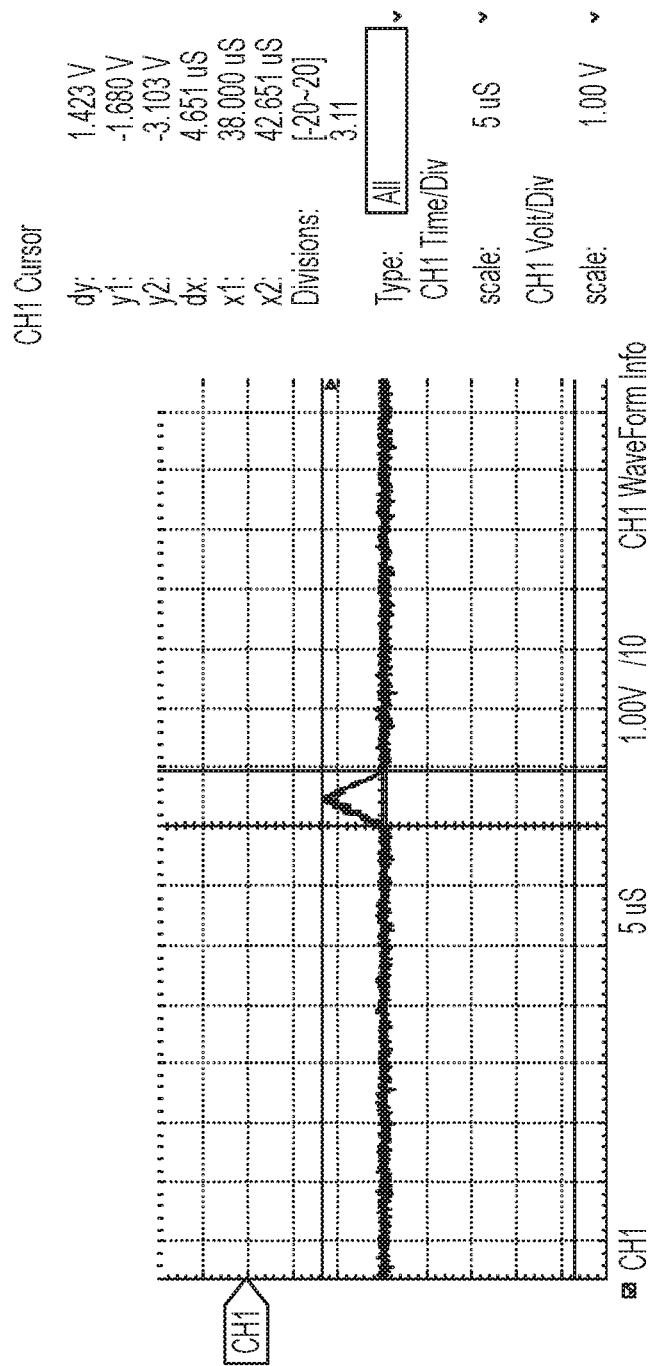
FIG. 2 illustrates an example plot of a sample event waveform output from a forward scatter detector.

In one embodiment of the present invention, the detection of separation bubble gaps is used in the accurate identification of individual sample wells. This may, in some cases, be used in addition or alternatively to the parameters already used. Separation bubble gaps are identified by analyzing the voltage output signal generated by a scatter detector, such as forward detector 124 or side scatter detector 128, of the flow cytometer as a flow stream with a plurality of separation-gas separated samples passes through the flow cytometer for a period of time. While the samples, each expected to contain particles of interest, in the flow stream are traveling through the flow cytometer flow cell, each event triggered by a particle generates a fairly consistent scatter waveform pattern having a time duration between about 4 μs and 10 μs and a peak to peak detector voltage output between about 1.4 to 1.6 volts. A sample event waveform obtained via an oscilloscope connected to the forward scatter detector output is shown in FIG. 2.

Figure 3:
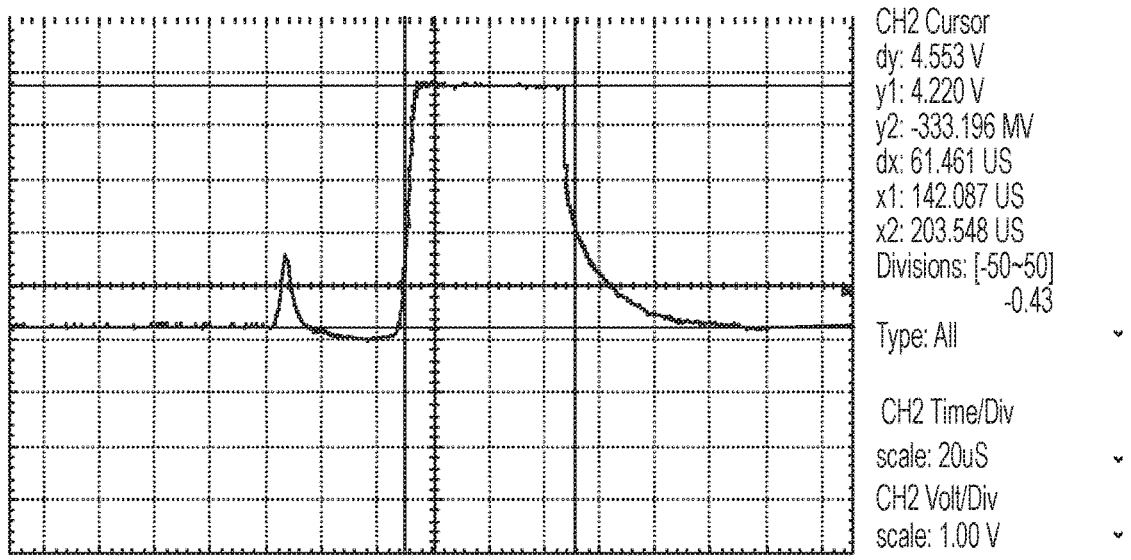
FIG. 3 illustrates an example plot of an air bubble gap waveform output from a forward scatter detector.
Figure 4:
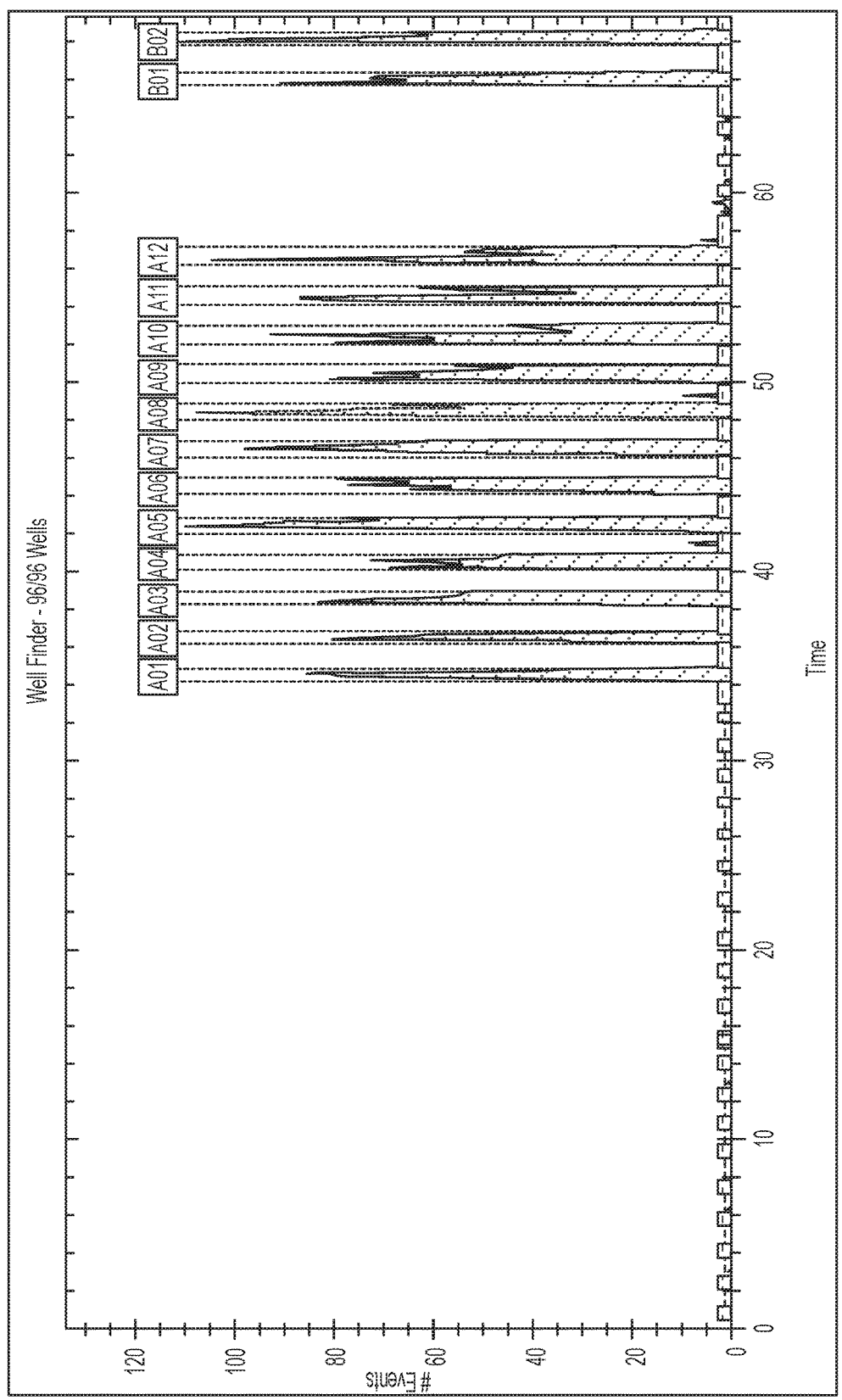
FIG. 4 illustrates an example histogram of sample event data of pre-plate prime air bubbles, the first row A of the sample plate with inter-row shake, and the first two wells of row B of the sample plate, acquired from the flow cytometer plotted with separation gas timing output data acquired from the forward scatter detector of the flow cytometer.

A separation bubble gap following a sample traveling through the flow cytometer flow cell also generates a fairly consistent scatter waveform pattern. The waveform pattern is show in FIG. 3 and has the characteristics of a time duration between 50 μs and 90 μs, which is about seven to nine times greater than a sample event waveform, and a peak to peak detector voltage output that is between about 4.2 to 4.8 volts, which is three times greater than a sample event waveform. As it goes through the flow cell, an air bubble acts as a mirror, reflecting a large portion of the excitation laser light to the forward scatter detector. This intensity of scattered light causes the detector to output a signal with the maximum voltage, as shown in the waveform.

Using these waveforms, a processor, integrated as part of or in communication with the flow cytometer, analyzes the voltage output over time to match one of the follow signal patterns: background (no event measured), an event measured, or an air bubble measured based on the waveforms described above. These patterns can then be used to identify each source well in the data stream.

In particular, the method for detecting a separation gas in a fluid flow stream comprises: (a) generating, with a scatter detector, a scatter voltage output signal indicative of an intensity of scattered light as a flow stream comprising a plurality of samples, each sample separated by a separation gas, passes through a flow cytometer for a period of time, (b) sampling the scatter voltage output signal, and (c) recording a timestamp and a voltage value for each sampled voltage of the scatter voltage output signal that is greater than a separation gap threshold. In one example, each of the plurality of samples is suspected of containing particles of interest. The method may also include comparing each sampled voltage of the scatter voltage output signal to the separation gap threshold.

In operation, the processor samples the voltage output signal of the scatter detector, and records voltage values that are greater than a separation gap threshold. In some examples, each sampled voltage of the voltage output signal is compared to the separation gap threshold. The separation gap threshold has, in some examples, a value at least two times greater than a maximum voltage output of the plurality samples, which can depend on the type of flow cytometer and the electronics of the forward scatter detector. In connection with the experimental data presented below, the maximum voltage capable of detection by the forward scatter detector is 5V and a separation gap threshold of 3.9V was selected (corresponding to (800/1023)*5V). This threshold is more than double the maximum expected sample output of 1.6V from the forward scatter detector. Further, the voltage output signal is sampled at a frequency. In some examples, the sampling frequency is between 5 kHz and 500 kHz. In a further example, the sampling frequency of up to about 10 MHz is used.

The analysis software algorithm, executed by the processor, can consist of two portions, an initial time correlation and an air bubble gap event timing, to delineate individual microplate wells from the continuous flow cytometer data stream. The bubble-gap event timing algorithm may be used in conjunction with other well identification parameters, such as those described above.

As scatter data is collected, a timestamp is recorded at the time that each sampled voltage that is over the threshold occurred. Therefore, the flow cytometry system, or the processor integrated therein or in communication therewith, may also include a clock. This timestamp will be used to correlate detected patterns with the data stream from the flow cytometer. The flow cytometry system may also include, or be in communication with a memory in which the sampled voltage values above the threshold and the timestamps are recorded.

In addition, at the start of a microplate sampling run, before the first microplate well is sampled, a starting time calibration sequence may be performed. In such an example, the method may also include prior to the generating step, moving the plurality of samples comprising particles into the flow stream, inserting the separation gas between adjacent ones of said plurality of samples to separate said samples from each other in said flow stream, said flow stream thereby constituting a gas-separated sample flow stream, guiding said fluid-separated sample flow stream including the separated samples and the separation fluid to and through the flow cytometer, and continuously operating the flow cytometer to focus the gas-separated flow stream and to detect scattered light by the scatter detector as the fluid flow stream passes through the flow cytometer. In such an example, the method may also include prior to the moving step, obtaining a plurality of samples from a plate having a plurality of sample wells, wherein each sample of the plurality of samples is obtained from a respective well of the plurality of wells.

In one particular example, three separation bubble gaps are introduced, each separated by a one second sip of deionized water, and followed by eight seconds of deionized water. When sample event data acquisition begins from the flow cytometer, the bubble-gap detector microprocessor is initiated with a time stamp of zero. With this calibration sequence, the timestamp output of the air bubble gap detector (separation gas timing data) can be correlated with the flow cytometer sample event data timing to synchronize the start of a plate sampling run. In operation, separation gas timing data generated from the captured scatter voltage signal and corresponding timestamp, which is applied when the output of the scatter detector is over the set voltage threshold. This separation gas timing data is synchronized with the sample events data from the flow cytometer based on timing. The separation gas timing data is plotted with the sample events versus time histogram that is used for well identification. Accordingly, the air bubble detection pattern timing output may be used to delineate between well air bubble gaps where microbubbles, debris, insufficient sample, sample preparation error or carryover would make it difficult to do so only using event counts over time.

In one example, the scatter detector comprises a forward scatter detector, as described in addition detail below in relation to FIGS. 4-8. In another example, the scatter detector comprises a side scatter detector as described in additional detail below in relation to FIG. 9. In the embodiment where the scatter detector comprises a forward scatter detector, the method may also include generating, with a side scatter detector, a side scatter voltage output signal indicative of an intensity of side scattered light as the flow stream comprising the plurality of samples, each sample separated by a separation gas, passes through the flow cytometer for the period of time, generating, with a fluorescence detector, a fluorescence voltage output signal indicative of an intensity of fluorescent light emitted as the flow stream comprising the plurality of samples, each sample separated by a separation gas, passes through the flow cytometer for the period of time, and generating sample events data based, at least in part on the forward scatter voltage output signal, side scatter voltage output signal and fluorescence voltage output signal.

Figure 5:
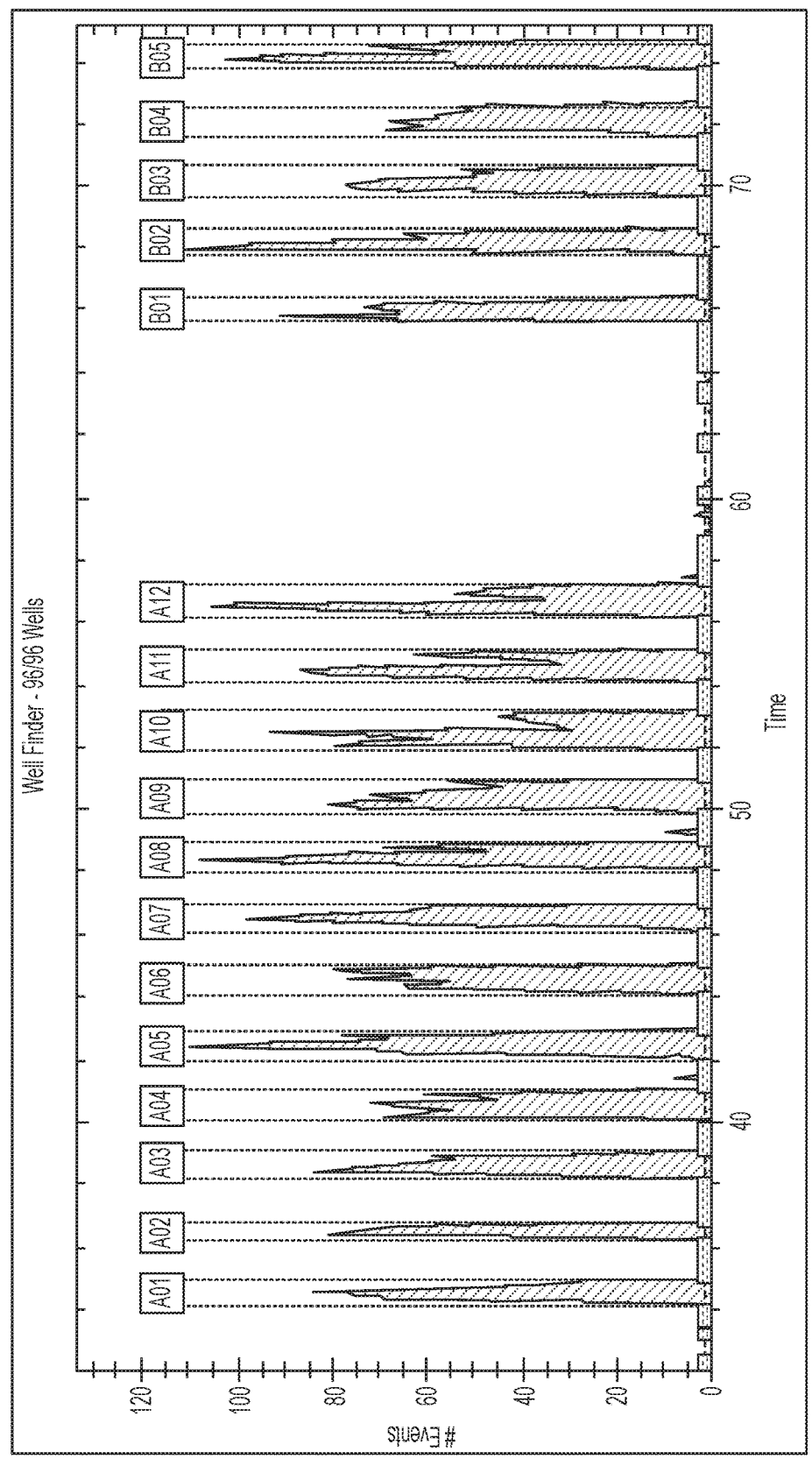
FIG. 5 is a zoomed-in view of a portion of FIG. 4.
Figure 6:
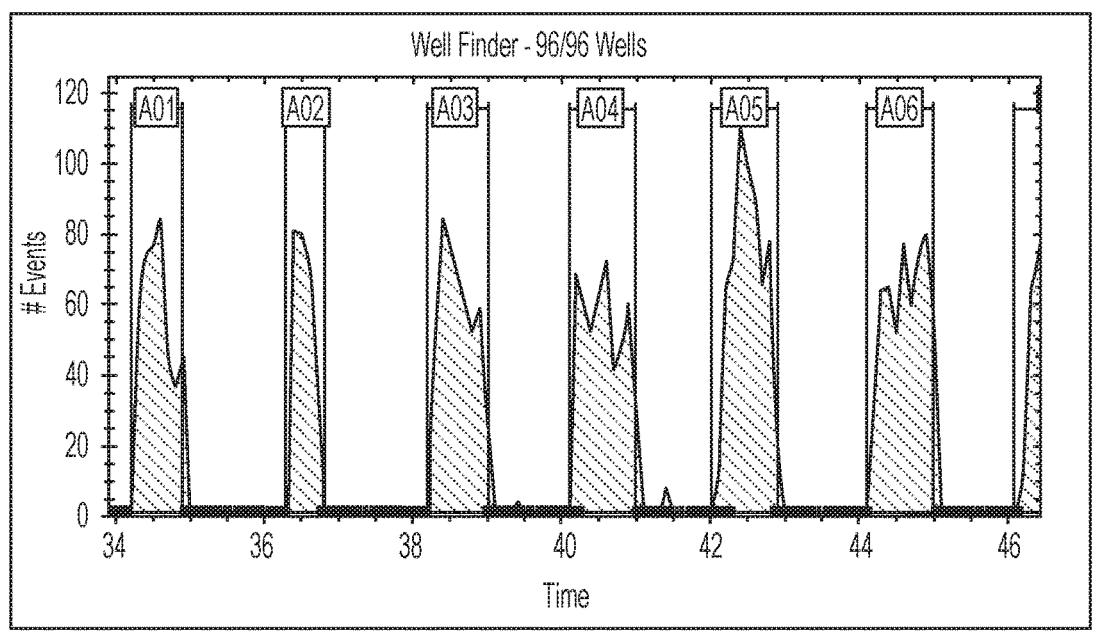
FIG. 6 is a zoomed-in view of a portion of FIG. 4.
Figure 7:
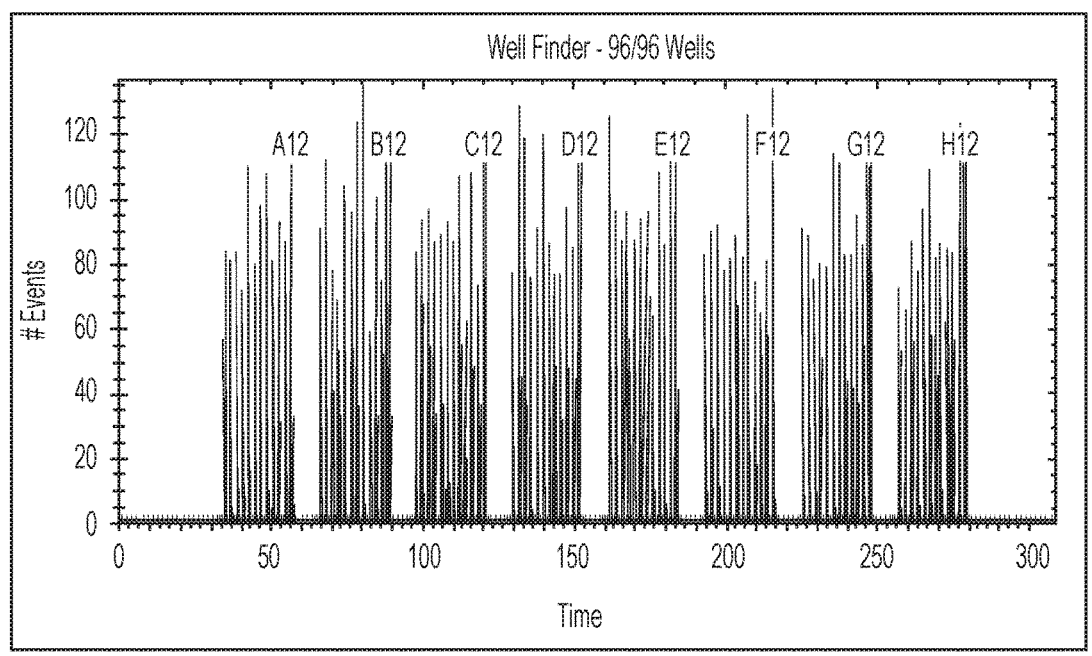
FIG. 7 illustrates an example histogram of sample event data of a full 96-well plate acquired from the flow cytometer plotted with separation gas timing output data acquired from the forward scatter detector of the flow cytometer.

An exemplary air bubble detector of the present invention was tested experimentally by first measuring forward scatter flow cytometer waveforms of both air bubbles and samples and determining a method to distinguish the two types of waveforms. The resulting separation gas timing data is illustrated in FIGS. 4-7, plotted with the sample detection data histogram. The flow cytometer generates sample detection data based on the outputs of the forward scatter, side scatter and fluorescence detectors. The number of wells identified by the well identification algorithm and the total number of wells in a sample plate are shown at the top of the histogram. In these figures, the tall vertical lines on the time histogram correlate to bubbles going through the flow cell and the short vertical lines correlate to the number of events in a sample. The detection of separation bubbles can be seen particularly well in the pre-plate priming sequence shown in FIG. 4, which also illustrates the detector output from sampling of the first row A of the well plate, followed by shaking of the microplate to resuspend any particles in the samples, with inter-row shake, and the detector output from sampling of the first two wells of row B. FIG. 5 is a close-up view of a portion of FIG. 4, specifically, the detector output from sampling of the first row A of the well plate, followed by microplate shaking, and the detector output from sampling of the first two wells of row B. FIG. 6 is also is a close-up view of a portion of FIG. 4, specifically the detector output from sampling of the first six wells of row A of the well plate. FIG. 7 is a histogram of the detector output from a sampled full 96-well plate. Control software for operating a flow cytometry device may, in some cases, allow a user to program a custom sampling protocol, which may include, for example, a set of probe rinses and/or microplate shaking sequences to be performed after a certain number of wells are sampled. In the illustrated examples, a 96 well microplate was sampled row-by-row, with microplate shaking after each row.

The gates, each labelled with a letter and number, in each of FIGS. 4-7 correspond to the respective wells of the well plates identified by the method of the present disclosure. This novel method utilizing the forward scatter output to detect bubble gaps limit well identification errors, as compared to previous methods. The forward scatter waveform analysis described herein, used in conjunction with the sampling protocol, may allow for accurate identification and verification of sampling protocol features, such as row or column plate shaking and probe rinses, as well as the bubble gaps between samples, independent of detection of the samples themselves. In the forward scatter waveform analysis, sequences of detected bubbles are used to delineate the samples, rather than sequences of low event counts between samples. This may eliminate possible errors that can occur where there are sequences of low event counts in a sample due to, for example, sample preparation error, incorrectly dispensed samples, samples with very few particles of interest (e.g., toxicity assays), insufficient re-suspension of the sample, clogging of the fluidic sample tubing. In addition, forward scatter waveform analysis can provide real-time feedback on the consistency of bubble gaps in the flow cell which can be used to detect clogging of the fluidic pathway from sample probe to flow cell.

Figure 8:
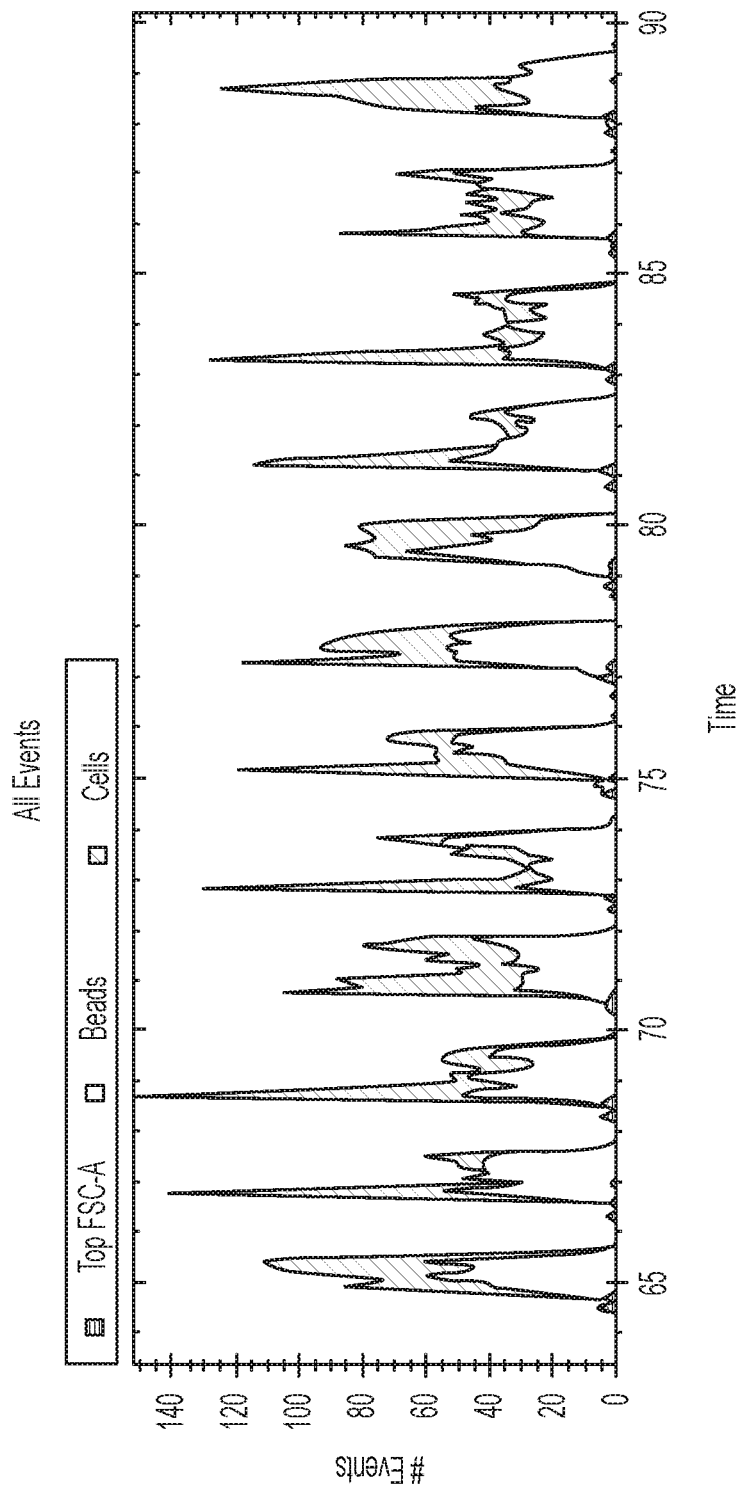
FIG. 8 illustrates an example histogram of sample event data of a processed FSC-A output acquired from the flow cytometer plotted with separation gas timing output data acquired from the forward scatter detector of the flow cytometer.

FIG. 8 illustrates an example histogram of sample event data of a processed FSC-A output acquired from the flow cytometer plotted with separation gas timing output data acquired from the forward scatter detector of the flow cytometer. As such, in the example shown in FIG. 8 the flow cytometer detector itself (not an external device) converts the voltage output from the forward scatter PMT to a processed FSC-A digital output value for each event. The boundary between the separation gas and the liquid sample will cause one or more events with a FSC-A value to be at the top limit of detection (e.g., top value produced by the flow cytometer), thereby forming gates around the top FSC-A event values as shown in FIG. 8. The flow cytometer also records a timestamp for every event recorded. With this information, the separation gas timing data is synchronized with the sample events data from the flow cytometer based on timing. The separation gas timing data is plotted with the sample events versus time histogram that is used for well identification. Accordingly, the air bubble detection pattern timing output may be used to delineate between well air bubble gaps where microbubbles, debris, insufficient sample, sample preparation error or carryover would make it difficult to do so only using event counts over time.

Figure 9:
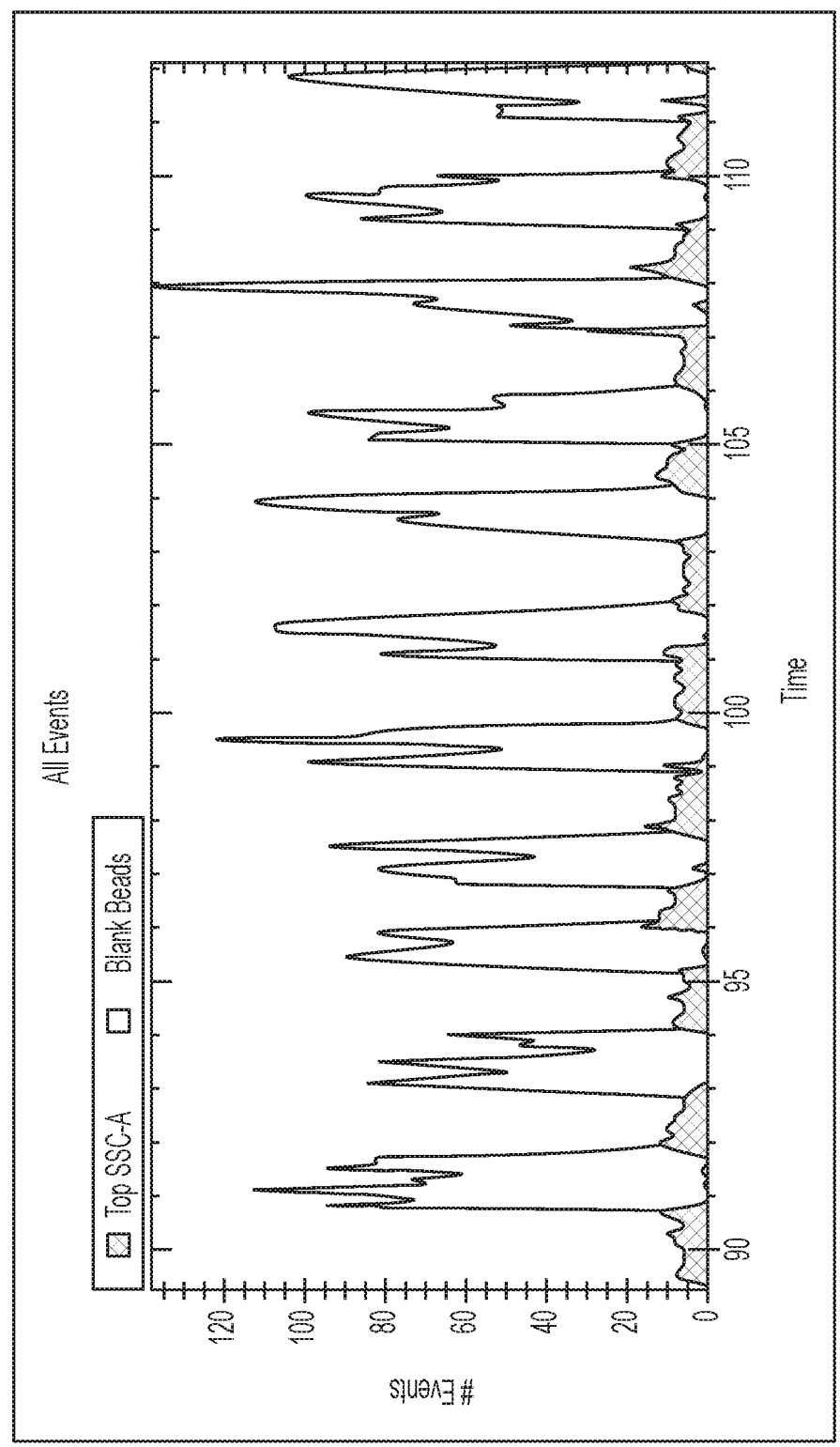
FIG. 9 illustrates an example histogram of sample event data of a processed SSC-A output acquired from the flow cytometer plotted with separation gas timing output data acquired from the side scatter detector of the flow cytometer.

FIG. 9 illustrates an example histogram of sample event data of a processed SSC-A output acquired from the flow cytometer plotted with separation gas timing output data acquired from the side scatter detector of the flow cytometer. In the example shown in FIG. 9, the flow cytometer detector itself (not an external device) converts the voltage output from the side scatter PMT to a processed SSC-A digital output value for each event. The flow cytometer also records a timestamp for every event recorded. With this information, the separation gas timing data is synchronized with the sample events data from the flow cytometer based on timing. The separation gas timing data is plotted with the sample events versus time histogram that is used for well identification.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A method for detecting a separation gas in a fluid flow stream comprising:
generating, with a scatter detector, a scatter voltage output signal indicative of an intensity of scattered light as a flow stream comprising a plurality of samples, each sample separated by a separation gas, passes through a flow cytometer for a period of time;
sampling the scatter voltage output signal; and
recording a timestamp and a voltage value for each sampled voltage of the scatter voltage output signal that is greater than a separation gap threshold, wherein the separation gap threshold has a constant value.

2. The method of claim 1, further comprising:
comparing each sampled voltage of the scatter voltage output signal to the separation gap threshold.

3. The method of claim 1, wherein the separation gap threshold has a value at least two times greater than a maximum voltage output of the plurality samples.

4. The method of claim 1, wherein the recording comprises storing in a memory.

5. The method of claim 1, wherein each of the plurality of samples is suspected of containing particles of interest.

6. The method of claim 1, wherein the timestamp comprises a time at which a sampled voltage greater than a separation gap threshold occurred.

7. The method of claim 1, wherein the sampling occurs at a frequency.

8. The method of claim 7, wherein the frequency is between 5 kHz and 500 kHz.

9. The method of claim 1, further comprising:
prior to the generating step, moving the plurality of samples into the flow stream;
inserting the separation gas between adjacent ones of said plurality of samples to separate said samples from each other in said flow stream, said flow stream thereby constituting a gas-separated sample flow stream;
guiding said fluid-separated sample flow stream including the separated samples and the separation fluid to and through the flow cytometer; and
continuously operating the flow cytometer to focus the gas-separated flow stream and to detect scattered light by the scatter detector as the fluid flow stream passes through the flow cytometer.

10. The method of claim 9, further comprising:
prior to the moving step, obtaining a plurality of samples from a plate having a plurality of sample wells, wherein each sample of the plurality of samples is obtained from a respective well of the plurality of wells.

11. The method of claim 10, further comprising:
generating separation gas timing data comprising the recorded a voltage value for each sampled voltage of the scatter voltage output signal that is greater than the separation gap threshold and the corresponding timestamp.

12. The method claim 10, further comprising:
identifying a respective sample well of the plurality of sample wells, based, at least in part, on the separation gas timing data.

13. The method of claim 1, wherein the scatter detector comprises a forward scatter detector.

14. The method of claim 1, wherein the scatter detector comprises a side scatter detector.

15. The method of claim 14, further comprising:
generating, with a side scatter detector, a side scatter voltage output signal indicative of an intensity of side scattered light as the flow stream comprising the plurality of samples, each sample separated by a separation gas, passes through the flow cytometer for the period of time;
generating, with a fluorescence detector, a fluorescence voltage output signal indicative of an intensity of fluorescent light emitted as the flow stream comprising the plurality of samples, each sample separated by a separation gas, passes through the flow cytometer for the period of time; and
generating sample events data based, at least in part on the forward scatter voltage output signal, side scatter voltage output signal and fluorescence voltage output signal.

16. The method of claim 1, further comprising:
correlating the separation gas timing data and the sample events data based, at least in part, on time.

17. The method of any of claim 1, further comprising:
plotting the correlated separation gas timing data and the sample events data.

18. A non-transitory computer readable medium having stored therein instructions that are executable to cause a processor to perform the method of claim 1.

19. A system comprising:
a flow cytometer comprising a scatter detector;
a processor in communication with the output of the scatter detector; and a non-transitory computer readable medium having stored therein instructions that are executable to cause the processor to perform the method of claim 1.

20. The system of claim 19, further comprising:
an autosampler for inserting a plurality of samples comprising particles from a plurality of respective source wells into a fluid flow stream.

21. The system of claim 20, wherein the flow cytometer is in communication with the autosampler via a conduit and is configured to focus the fluid flow stream delivered by the conduit from the autosampler and selectively analyze the particles in each of the plurality of samples as the fluid flow stream passes through the flow cytometer.

22. The system of claim 20, further comprising:
a pump for moving the plurality of samples in the fluid flow stream along said single length of tubing,
the autosampler and the pump cooperating to introduce aliquots of a separation fluid between successive ones of the samples in the fluid flow stream to configure the fluid flow stream as a bubble-separated fluid flow stream.

23. The system of claim 19, wherein the scatter detector comprises a forward scatter detector, and wherein flow cytometer further comprises a side scatter detector and a fluorescence detector.

* * * * *